United States Patent [19]

Georges

[11] 4,367,915
[45] * Jan. 11, 1983

[54] AUTOMATIC MICROSCOPE SLIDE

[76] Inventor: Michael P. Georges, P.O. Box 800, Norwood, Mass. 02062

[*] Notice: The portion of the term of this patent subsequent to Feb. 3, 1997, has been disclaimed.

[21] Appl. No.: 228,762

[22] Filed: Jan. 26, 1981

Related U.S. Application Data

[63] Continuation of Ser. No. 920,157, Jun. 29, 1978, Pat. No. 4,248,498, which is a continuation of Ser. No. 746,617, Dec. 1, 1976, abandoned.

[51] Int. Cl.³ .............................................. G02B 21/26
[52] U.S. Cl. .................................................... 350/530
[58] Field of Search ...................... 350/86–92, 350/81, 95; 356/244; 353/27 A, 116; 221/88; 414/403, 417

[56] References Cited

U.S. PATENT DOCUMENTS

| | | | |
|---|---|---|---|
| 3,361,031 | 1/1968 | Stroud | 350/87 |
| 3,528,735 | 9/1970 | Bluitt et al. | 350/27 A |
| 3,738,730 | 6/1973 | Binnings et al. | 350/90 |
| 3,851,972 | 12/1974 | Smith et al. | 350/81 |

Primary Examiner—Jon W. Henry
Attorney, Agent, or Firm—George W. Neuner

[57] ABSTRACT

An automated microscope specimen slide examination system processes a plurality of microscope specimen slides one at a time for microscopic examination. A specimen slide storage magazine is indexed to position each specimen slide for access by a horizontal feed mechanism which transfers the specimen slide onto a microscope stage which has controllable X, Y and Z axis positioning to move the specimen slide into the optical viewing field of the microscope, focus the image and conduct systematic examination over the desired area of the specimen by X-Y axis incremental motion. At the end of the examination the specimen slide is returned to the magazine and the procedure is repeated for the next specimen slide. Previously examined specimen slides that have been returned to the storage magazine may be automatically returned to the microscope stage for reexamination.

12 Claims, 6 Drawing Figures

AUTOMATIC MICROSCOPE SLIDE

This is a continuation of application Ser. No. 920,157 filed June 29, 1978, now U.S. Pat. No. 4,248,498, which is a continuation of application Ser. No. 746,617 filed Dec. 1, 1976 now abandoned.

BACKGROUND OF THE INVENTION

Microscopes are widely used for the examination of biological and mineral specimens and often, as in the medical field, it is desirable to regularly examine large quantities of specimens such as the blood of hospitalized patients. In such cases, electronic systems may be used to automatically examine and analyze the optical images of the microscope. Where electronics systems are used for rapid analysis of microscope specimen images it becomes desirable to automatically regularly and rapidly feed the specimens to the microscope optics. After analysis a specimen would be removed to make room for the next specimen and would be collected for either further examination, reference, record keeping or disposal.

A microscope specimen stage is the platform of the microscope which supports and carries the object to be examined. If the object to be examined is to be viewed with transmitted light then it is necessary for the specimen stage or support to have a light transmissive opening in alignment with the microscope objective lens light path. The specimen stage has this opening for light transmission in or near its center. In order that as much area of the specimen slide as possible be viewed during examination of the specimen without sliding it about the specimen stage this opening in the specimen stage is made as large as possible and exposes the full width of the specimen slide. If the specimen slide were pushed onto the specimen stage while the specimen stage was positioned in the light path of the objective and condenser lenses the specimen slide would drop into this opening.

Specimen slides for use with microscopes at present are generally made of transparent glass. This glass is extremely brittle and chips, abrades, and fractures very easily. What might otherwise be considered normal and safe procedures for handling and clamping most other materials are generally not satisfactory for glass microscope specimen slides. The scraping action and the abrasiveness of the glass edges will quickly deteriorate and make useless many of the metal and plastic surfaces contacted by it if excessive rubbing pressure is applied. Because of these scraping, chipping, fracturing and abrasive characteristics the glass microscope specimen slide must be handled gently and carefully. Heavy clamping of the glass surfaces and applying excessive surface and side pressures on it should be avoided. When moving the specimen slide about, excessive rubbing of the glass edges against metal and plastic surfaces should be avoided.

No matter how it is avoided elsewhere, clamping and guiding of the glass specimen slide cannot be avoided on the microscope specimen stage. If the specimen slide is to be seated securely and aligned properly it must be guided into position accurately and then clamped, but this clamping must be done as gently as possible.

SUMMARY OF THE INVENTION

The automated microscope specimen slide system of the present invention automatically takes microscope specimen slides one at a time from a storage magazine and places them onto the microscope specimen stage in an area adjacent to the objective and condenser lens system and then the specimen stage moves horizontally and carries the specimen slide into the optical light path of the microscope objective lens for viewing. The viewing is generally done electronically without operator intervention except where the operator wishes to check or review a specific item. Once the specimen slide is in the optical light path of the microscope objective lens a signal generated by the microscope viewing electronics will activate the specimen stage assembly Z axis focusing control motor and move the microscope stage in a vertical direction until the specimen is in focus. Other signals generated by the system electronics will activate the X and Y axis positional control motors and accurately move the specimen slide about the horizontal examination plane and place the specimen in any position or series of positions required for examination of the specimen. Focusing of the specimen during these positional changes is automatically corrected by the microscope viewing electronics control signals if required.

The specimen slide is pushed onto the microscope specimen stage from the magazine in which slides are stored to a position in which the specimen slide selected from the magazine is adjacent to the objective and condenser lens system and out of the optical light path. The specimen stage opening in this adjacent position is bridged by a structural member temporarily positioned such that the specimen slide can be pushed onto the specimen stage when supported by the temporary filler. After the specimen slide is seated the loaded specimen stage then moves into the light path of the objective and condenser lenses for viewing of the specimen while the filler stays behind and remains out of the optical field of view.

In the embodiment shown the specimen slide is placed directly onto the microscope stage which is positioned in the loading area and waiting for the specimen slide to arrive and be deposited upon it. An alternative would be for the specimen slide to be placed in the loading area when the microscope stage is not there but is elsewhere in an adjacent position. Then the microscope stage would move from this adjacent position to the specimen slide loading position and pick up and retain the waiting specimen slide.

Once the examination of the specimen is completed the specimen slide is removed in order to make room for the next one. The specimen slide is put back into the magazine but could be channeled elsewhere if desired. When the specimen slide has been placed back into the specimen slide magazine or otherwise removed from the specimen slide feed path then the magazine will automatically index to bring the next specimen slide into position for dispensing or feeding. The cycle is then continued and the next specimen slide is fed to the microscope specimen stage for observation.

After the examination of a particular series of specimen slides has been completed any individual specimen slide that requires re-examination can by either operator signals or by predetermined control signals be fed automatically back into the microscope viewing optics for further examination.

The object of the invention is to provide an improved automatic microscope specimen slide examination system having the foregoing features and advantages.

DESCRIPTION OF THE PREFERRED EMBODIMENT

Figure 1:
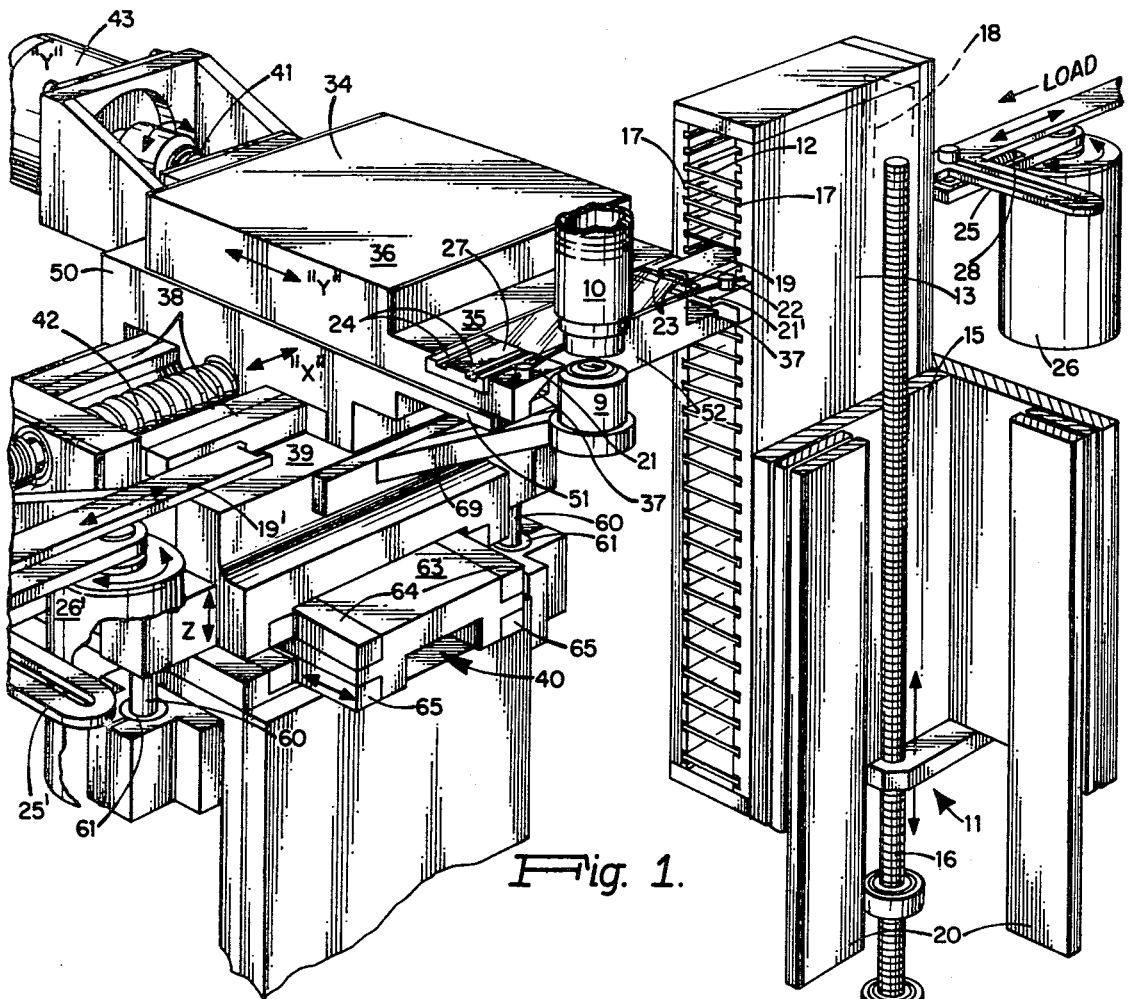
FIG. 1 is a partial perspective view of the overall specimen slide storing, feeding, and X-Y-Z axis translation and positioning portions of the microscope stage system of the invention.

Referring now to the drawings showing the preferred embodiment of the invention, the apparatus is oriented such that the specimen slide is always in an essentially horizontal plane except where slight longitudinal tilting may be used during the specimen slide transfer. This constant essentially horizontal position of the specimen slide makes optimum use of gravity for locating, restraining, and holding the specimen slide in place. Heavy clamping is avoided and where clamping is required only light gentle pressures are applied. Also, excessive pressures in sliding the specimen slide into spring loaded clips or clamps is avoided since the rubbing action has a detrimental abrasive eroding action on the glass edges and corners and on the surfaces of the materials contacted. However, where spring loaded guides and clips are used light pressures and low incidence contact angles are used.

SPECIMEN SLIDE MAGAZINE INDEXING ASSEMBLY

The specimen slide magazine indexing assembly generally designated 11 has a group of specimen slides 12 that are retained and grouped in a spaced apart relationship within a magazine 13. A control drive motor 14 indexes the magazine 13 successively so that the specimen slides 12 may be properly dispensed to the microscope specimen stage 35 in specific order or sequence. After examination the specimen slides 12 are returned to the magazine 13 in the embodiment shown.

After the transparent glass specimen slides 12 have been prepared with the object to be examined they are placed in the magazine 13 as shown. The magazine 13 may be designed to hold an convenient number of specimen slides, for example 60. The magazine is used primarily as a temporary storage station from which to dispense and then recover specimen slides during the examination process but may also be used for long term storage.

Once loaded with prepared specimen slides 12 the magazine 13 is placed into a magazine support bracket 15 which is mounted on vertical ball bearing slides 20 and is in threaded engagement with a lead screw 16 which may be of the recirculating ball type driven by control motor 14. Magazine 13 is secured in place by suitable retaining means such as detents, not shown. When the magazine 13 is in place in the magazine indexing assembly 11, the specimen slides 12 within the magazine are in a horizontal plane. The specimen slides 12 are supported loosely in grooves 17 formed on the interior of the magazine 13, and, if desired, may be restrained in the magazine by lightly tensioned spring clips (not shown). These spring clips may contact either the face or the edges of the specimen slides (or both) when the specimen slides are in the grooves 17. These grooves 17 are open at one end at the front of the magazine to permit discharge of the specimen slides 12 for transfer to the microscope stage 35. An elongated vertical opening 18 is provided in the rear of the magazine 13 to permit a push bar 19 to enter and contact the back edge of the selected specimen slide 12 and slide it onto the specimen stage 35 of the microscope. The front of the magazine 13 is open to allow the specimen slide entry into and exit from the magazine, but a thin cover (not illustrated) may be placed on the front of the magazine after loading to act as a dust cover and to prevent accidental spillage during handling. This thin cover is slipped off when the magazine is inserted into the magazine support bracket and may be slipped on again when the magazine is to be removed.

Magazine indexing is preferably electronically controlled and programmed to rapidly position each specimen slide for dispensing in successive order or any other sequence by the slide transfer mechanism.

Other specimen slide storage receptacles than the described magazine may be used and other specimen slide indexing or positioning techniques such as a gravity feed may be used for placing the specimen slides into the dispensing or feeding position. These alternative methods however will generally lack the flexibility of the described system which permits dispensing of specimen slides in any sequence desired and which also permits review of any number of previously examined specimen slides and in any order desired.

SPECIMEN SLIDE TRANSFER MECHANISM ASSEMBLY

There are two specimen slide transfer mechanisms used, one to push the specimen slide 12 from the specimen slide magazine 13 onto the microscope stage specimen slide seat 21 and 21' and the other to push the specimen slide 12 back into the magazine 13 after it has been examined. An alternative transfer mechanism could provide a single mechanism in a push to load and then pull to unload arrangement instead of the present push to load and then push to unload arrangement.

After the specimen slide magazine 13 has indexed to a specimen slide dispensing position the push bar 19 enters through the rear opening 18 of the magazine 13 to contact the back edge of the specimen slide 12 and slides the specimen slide 12 into the microscope stage slide seat 21 and 21'. The push bar 19 which contacts the end of the specimen slide 12 has a channel shape with the flanges 23 of the channel pointing down. A cutout 22 makes the end of push bar 19 contact the specimen slide 12 at two points. The flanges 23 of the push bar channel section are longer than and overlap the thickness of the specimen slide 12 that they push against. This is to insure full contact between the push bar and the end of the specimen slide. Grooves 24 are provided in the microscope specimen stage 35 to allow clearance of the push bar channel flanges 23.

The pushing motion for the specimen slide 12 is essentially rectilinear and may be either essentially constant in speed or it may have a controlled acceleration upon starting the specimen slide transfer and a controlled deceleration upon bringing the specimen slide to rest at the end of its travel. Controlling the acceleration and deceleration of the specimen slide transfer is useful in minimizing the inertia effects of sudden starts and stops during the faster specimen slide transfer rates.

The push bar 19 may be actuated by any suitable linear motion device such as a scotch yoke or cam, rack and pinion gears or a screw and nut that is coupled to a drive means. In the embodiment shown a partial scotch yoke 25 and partial revolution reversible drive motor 26 are used.

Figure 6:
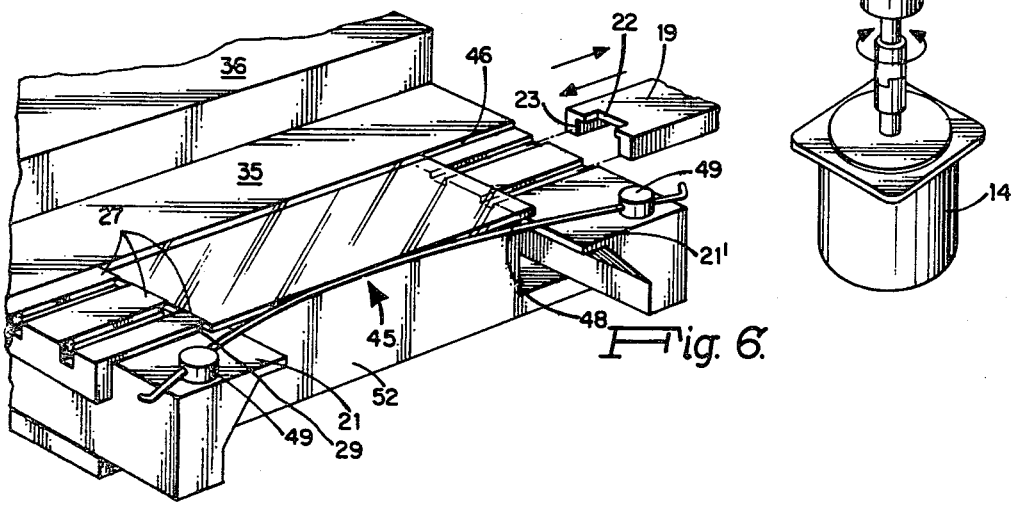
FIG. 6 is a partial perspective view showing details of the specimen slide stage.

Insertion of the specimen slide 12 into seated and retained position on the stage seats 21, 21' is best illustrated in FIG. 6 where a fixed edge guide 46 and spring clamping edge guide means 48 are provided. The means 48 is a bowed spring wire 18 slidably supported in transverse openings in posts 49 which are mounted on the projections of stage 35. Upon entry of a specimen slide one edge thereof contacts spring wire 48 with a low angle of incidence and the flexing of wire 48 urges the other edge of the specimen slide against fixed edge guide 46. The inserting motion proceeds until the slide engages end stop 27 which may be undercut as at 50 to positively retain the specimen slide.

The specimen slide 12 is pushed up against the specimen stage slide end stop 27 with spring loaded means 28 provided in the scotch yoke drive 25 to allow the push bar 19 to push the specimen slide 12 firmly into the end stop 27 without crushing it or excessively impacting it. After the push bar 19 has completed its forward push of the specimen slide 12 (and dwell if a dwell is used), then a reverse drive by motor 26 reverses the direction of the push bar linear motion actuator 25 to move the push bar 19 back to its starting position.

Figure 2:
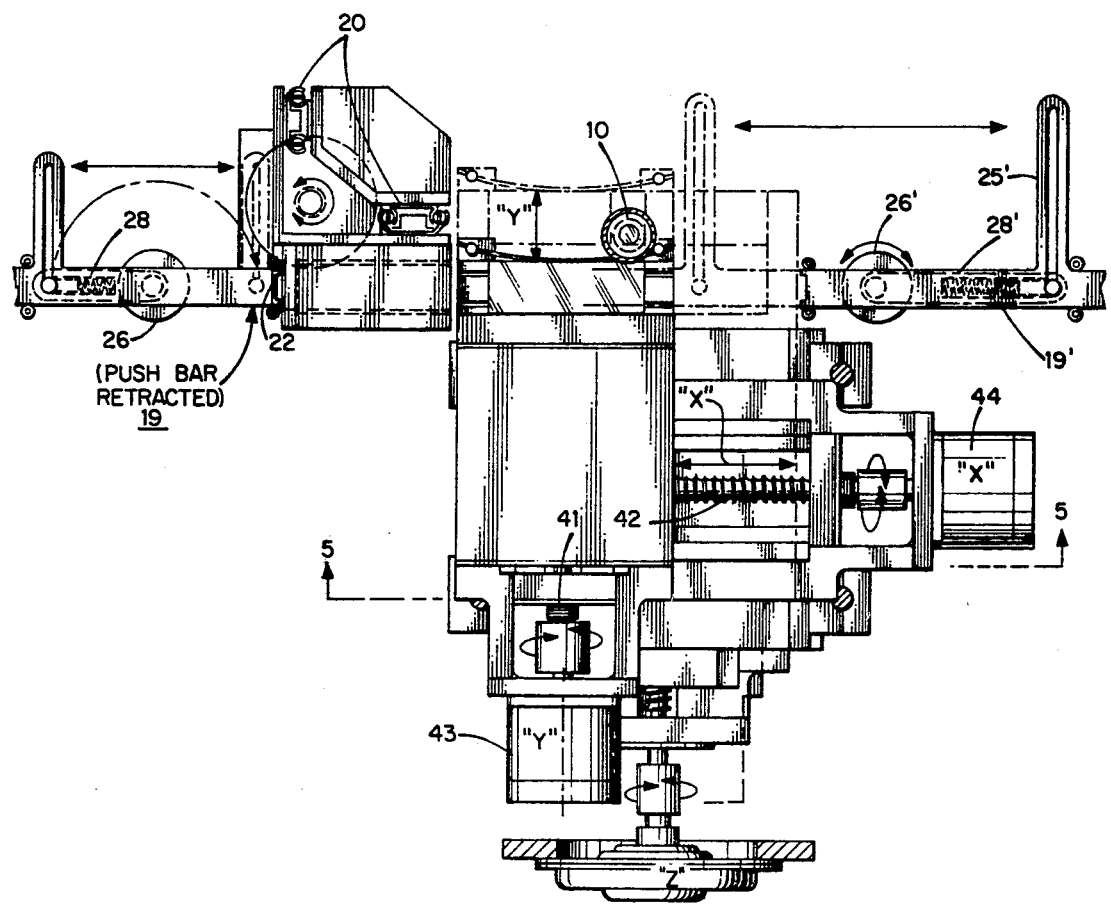
FIG. 2 is a top plan view of the apparatus shown in FIG. 1 including parts not shown in FIG. 1.
Figure 3:
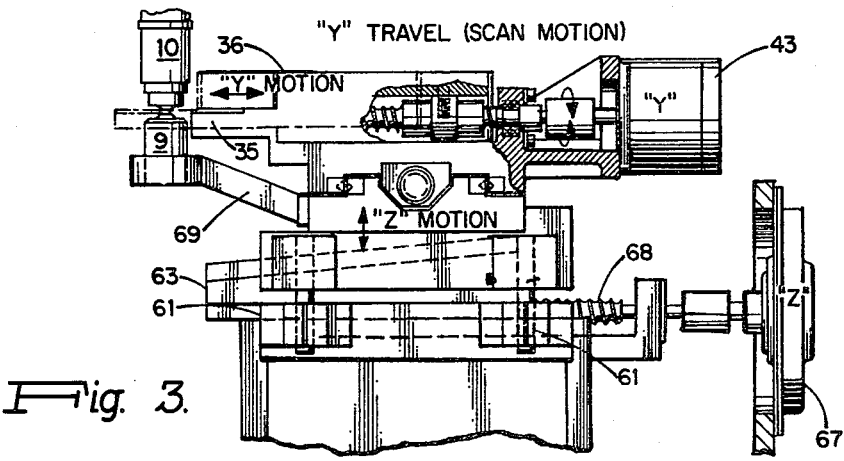
FIG. 3 is a right elevation view corresponding to FIG. 2 partially broken away to show the Y and Z axis translation and positioning drives with the extent of Y axis motion shown in phantom.
Figure 4:
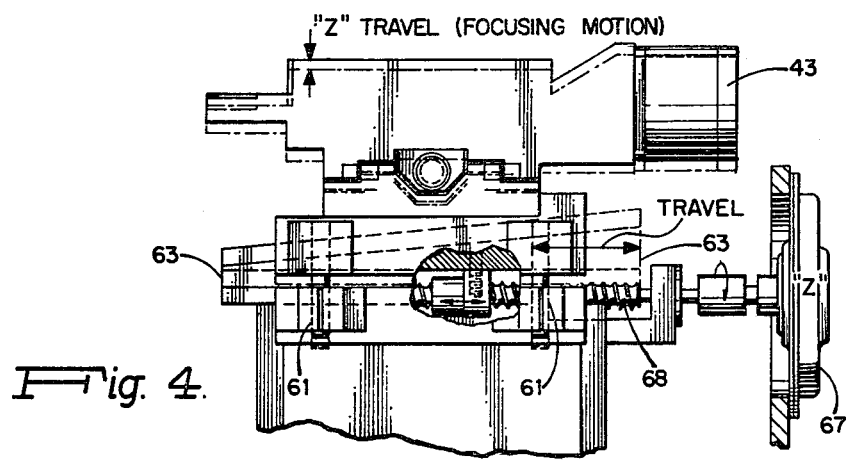
FIG. 4 is a view similar to FIG. 3 with other parts broken away to show the extent of focusing or Z axis travel.
Figure 5:
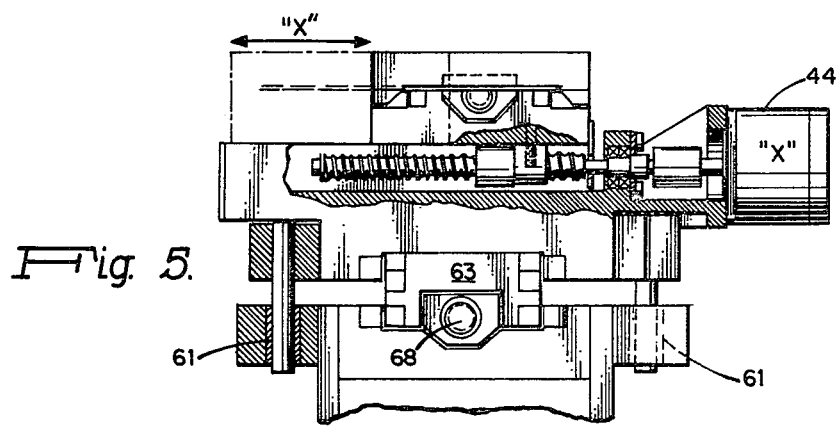
FIG. 5 is a rear elevation view partially in section taken approximately along 5—5 of FIG. 2.

To remove the specimen slide 12 from the microscope specimen stage 35 a corresponding push bar mechanism (operating left to right in FIG. 2) comprises push bar 19', partial scotch yoke 25' and motor 26' energized as desired to return the specimen slide 12 to the magazine 13.

MICROSCOPE STAGE POSITIONER ASSEMBLY

The microscope stage positioner assembly comprises a specimen slide stage 35 mounted on a precision motorized X-Y axis positioner assembly 34 for moving and positioning the specimen along a horizontal plane along with motorized up and down Z axis movement for specimen focusing.

The sliding member 36 of X-Y axis positioner assembly 34 is mounted for sliding motion in the Y direction relative to the combined Y axis base and X axis sliding member 50 by means of roller bearing linear slides 37. The combined Y axis base and X axis sliding member 50 in turn is mounted for motion in the X direction by means of roller bearing linear slides 38 mounted on a combined X axis base and Z axis moving member 39. The precision crossed roller bearing linear slides 37, 38 provide for precision low friction linear motion when the Y and X axis sliding members 36 and 50 are driven respectively by precision ball bearing screws 41, 42 which are rotated by stepping control motors 43, 44 for power and position control. The entire X—Y axis positioner assembly is supported on a Z axis positioner assembly 40 which is driven in the vertical direction as hereinafter described.

The specimen stage 35 protrudes out from the Y axis slide positioner sliding member 36 and has a wide opening 45 in its center shown occupied by filler 52 in FIGS. 1 and 6. Upon Y axis motion to place the specimen slide 12 between condenser lens 9 and objective lens 10 the filler 52 remains behind and the opening 45 exposes the maximum area of the specimen slide transparent surface to illumination for optical observation.

The specimen stage 35 has an edge guide 46 and an end stop 27 which assist to constrain and position the specimen slide 12 during loading onto the specimen stage 35. The end stop 27 may have a slight inverted bevel to help retain and push the specimen slide 12 downward against the stage support surfaces.

During transfer to the specimen stage 35 the specimen slide 12 is guided into and clamped against the edge guide 46 and retained against end stop 27 by an elongated bow-shaped spring 48 which is mounted by slidably projecting through horizontal bore holes in posts 49 projecting upward from the protruding ends of specimen stage 35. As a specimen slide 12 is driven by push bar 19 the leading corner and edge engage the bow spring 48 at a low angle of incidence. Progression of the specimen slide 12 toward its seated position flexes the bow spring 48 by deflecting it from the path of one edge of the specimen slide 12, the other edge of which is referenced against the edge guide 46. The bow spring 48 thus applies a small transverse force to the edge of the specimen slide 12 contacted to maintain the specimen slide 12 positioned against edge guide 46. At the end of the travel of push bar 19, the specimen slide 12 is accurately positioned against end stop 27 and edge guide 46 and retained in that position by the slight pressure exerted by bow spring 48 against the free edge of the specimen slide 12.

An extended portion 51 of the X axis positioner sliding member 50 has an upwardly extending surface 52 which serves as a bridge or filler for the specimen stage center opening 45. This filler 52 is functional only when the Y axis positioner sliding member 36 is in its retracted position with the specimen stage 35 removed from the viewing area of the microscope objective lens 10. After a specimen slide 12 is loaded into position on the projecting supports that form the specimen slide seats 21 and 21' of specimen stage 35 the Y axis positioner sliding member 36 is extended by Y axis drive motor 43 to move the specimen stage 35 outward and into the microscope objective lens viewing field. The filler 52 remains behind thereby uncovering the center opening 45 in the specimen stage 35 and exposing maximum specimen slide area to the optical viewing field. This filler 52 is the specimen slide loading position prevents the specimen slide 12 from falling through the specimen stage opening 45 during the specimen slide loading and unloading operation.

After the specimen slide 12 is positioned between the condenser lens 9 and objective lens 10, focusing is accomplished by raising and lowering the X-Y axis positioner assembly base 39. The base 39 is constrained to vertical motion by four rod guides 60 which project through linear recirculating ball bearings 61 which prevent any lateral motion but permit up and down movement. A horizontally moving inclined plane wedge 63 rides on roller bearing linear slides 64, 65 and is attached to an actuator screw 68 that is driven by a servo control motor 67. The wedge 63 vertically positions the Z axis positioner moving member 39 which is supported thereon by an under surface inclined to slide on the surface of the wedge 63. A servo signal from the microscope optics electronics will activate the servo control motor 67 to turn the screw 68 and drive the wedge 63 horizontally in or out thereby raising or lowering the assembly comprising combined Z axis moving member and X axis base 39, combined X axis moving member and Y axis base 50, Y axis moving member 36 and specimen stage 35 for focusing. The servo control motor 67 may be geared for any desired speed reduction.

The condenser lens 9 is attached to the base of the X axis positioner base 39 by bracket 69. This base and thus the condenser lens 9 does not move laterally in the X-Y horizontal plane but does move up and down in the Z axis with the focusing adjustment.

An alternative to the horizontally moving screw driven wedge used for focusing would be for the X-Y axis positioner assembly to be raised up and down for focusing directly by either a vertical lead screw or rack and pinion. The lead screw or rack and pinion might obtain any additional motion reduction required for fine or accurate focusing by being driven by a gear train.

As previously described, the microscopic examination of the specimen slide can take place either visually or automatically by well known techniques such as cell counting. For this purpose the X and Y positioning systems can be controlled manually or automatically. Thus after focusing by operating the Z-axis drive 67, the specimen slide carried by the stage may be moved to any desired location relative to the optical axis by actuation of the Y-axis drive 43 and the X-axis drive 44. For automatic examination the drives 43, 44 would be energized under scan or other program control.

Upon completion of the examination of a slide the horizontal positioning Y-axis drive returns the specimen slide on the stage to the position over filler 52 to permit push rod 19' to drive the slide back to storage position in the magazine, as previously described.

The operation of the disclosed embodiment will now be clear to those skilled in the art. While a particular embodiment has been disclosed, many modifications thereof which, without being limited thereto, include those suggested herein, will be apparent and are to be considered as within the scope of the invention which is defined by the appended claims.

I claim:

1. A bio-medical microscope specimen slide positioning apparatus adapted for use in automatic sequential examination of a group of microscope specimen slides and comprising:

a storage magazine for storing a plurality of said microscope specimen slides; means for said magazine operable for indexing a specimen slide to a specimen slide exit or entry position; specimen slide transfer means positioned relative to said storage magazine for removing and transporting from said magazine said specimen slide located in said magazine and positioned at said specimen slide exit or entry position; a microscope specimen slide stage for receiving a specimen slide from said magazine; means for positioning and retaining said specimen slide on said specimen slide stage; translation means for moving and positioning said stage with a specimen slide supported thereon in a geometric plane; and means for mounting to the apparatus a microscope optical viewing system in a disposition adjacent to said retained specimen slide such that by operation of said translation means said specimen slide can be moved about and positioned in the optical axis of said optical viewing system for optically examining the specimen on said specimen slide; said specimen slide transfer means including means positioned relative to said stage for removing said specimen slide from said stage after microscope examination.

2. Apparatus according to claim 1 and further comprising a substage condenser lens system operable for focusing on and directing concentrated light through said stage retained specimen slide at the area of said specimen slide being examined and into said microscope optical viewing system: and an objective lens assembly of said microscope optical viewing system positioned to receive the concentrated light directed through the stage retained specimen slide and into said microscope optical viewing system by said substage condenser lens system.

3. Apparatus according to claim 2 and further comprising means for focusing said microscope optical viewing system on the specimen slide when said specimen slide is retained by said stage.

4. Apparatus according to claim 1, wherein said translation means serves to move said stage in a horizontal plane and there is provided further positioning means supporting said translation means and operable for moving said stage with a specimen slide supported therein vertically.

5. Apparatus acording to claim 1, wherein said positioning means comprises an X-Y axis table with an upper slide assembly and a lower slide assembly, each said slide assembly being composed of an upper movable member and a lower stationary member and said lower slide assembly supporting said upper slide assembly at a right angle to said lower slide assembly for slidable motion along rectangular co-ordinates.

6. Apparatus according to claim 1, wherein said specimen slide transfer means includes a bar for engaging the end of a specimen slide.

7. Apparatus according to claim 1, wherein said storage magazine is vertical and has horizontal grooves for loosely retaining said specimen slides, an opening in one end of said grooves for entry and exit of said specimen slides, a stop at the other end of said grooves to position and retain said specimen slides and an opening in said storage magazine for said specimen slide transfer means to enter and engage and then project a specimen slide out of said storage magazine.

8. Apparatus according to claim 1, wherein said specimen slide transfer means for projecting a specimen slide out of said storage magazine has controlled smooth motion acceleration and deceleration means.

9. Apparatus according to claim 1, wherein said specimen slide transfer means further includes end means for pushing said specimen slide on said specimen slide stage back into said magazine.

10. Apparatus according to claim 1, wherein said storage magazine, said microscope specimen slide stage and said microscope optical viewing system (when mounted to the apparatus) are positioned directly adjacent to each other so as in use of the apparatus to enable transfer of the specimen slide projected form said magazine into the optical axis of said optical viewing system in a minimal span of distance.

11. Apparatus according to claim 1, and including a supporting structure for use in transporting said specimen slide to the microscope specimen slide stage loading position and adapted so that, in use of the apparatus, said supporting structure remains behind as the loaded specimen slide stage moves the specimen slide, in use of the apparatus, into the optical axis of said microscope optical viewing system.

12. Apparatus according to claim 1 wherein said specimen slide transfer means includes means for absorbing the over-travel motion so as not to break said specimen slide at the end of said specimen slide transfer movement of specimen slide stage.

* * * * *